(12) United States Patent
Vladiskovic et al.

(10) Patent No.: US 8,362,260 B2
(45) Date of Patent: Jan. 29, 2013

(54) CRYSTALLINE FORMS OF DEXLANSOPRAZOLE

(75) Inventors: Chiara Vladiskovic, Milan (IT); Gabriele Razzetti, Sesto San Giovanni (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 320 days.

(21) Appl. No.: 12/693,539

(22) Filed: Jan. 26, 2010

(65) Prior Publication Data
US 2010/0204479 A1  Aug. 12, 2010

(30) Foreign Application Priority Data

Feb. 6, 2009 (IT) .............................. MI2009A0157

(51) Int. Cl.
*C07D 401/12* (2006.01)
(52) U.S. Cl. .................................................. 546/273.7
(58) Field of Classification Search ................ 546/273.7
See application file for complete search history.

(56) References Cited

U.S. PATENT DOCUMENTS

| 6,462,058 | B1 | 10/2002 | Fujishima et al. |
| 7,285,668 | B2 | 10/2007 | Hashimoto et al. |
| 2004/0048898 | A1 | 3/2004 | Fujishima et al. |
| 2004/0049045 | A1 | 3/2004 | Hashimoto et al. |
| 2011/0028518 | A1 * | 2/2011 | Kolla et al. ............. 514/338 |

FOREIGN PATENT DOCUMENTS

| AU | 88406/91 | 6/1992 |
| EP | 1277752 A1 | 1/2003 |
| EP | 1293507 A1 | 3/2003 |
| EP | 1552833 A1 | 7/2005 |
| EP | 1607395 A1 | 12/2005 |
| WO | 03082857 A2 | 10/2003 |
| WO | 2009088857 A1 | 7/2009 |

* cited by examiner

*Primary Examiner* — Patricia Morris
(74) *Attorney, Agent, or Firm* — Rothwell, Figg, Ernst & Manbeck, P.C.

(57) ABSTRACT

The present invention relates to novel crystalline forms of Dexlansoprazole and a process for the preparation of amorphous Dexlansoprazole.

5 Claims, 9 Drawing Sheets

Fig. 1 XRPD of Dexlansoprazole form A

Fig. 3 DSC thermogram of Dexlansoprazole form B

Fig. 5  XRPD of Dexlansoprazole form D

Fig. 7 XRPD spectrum of amorphous Dexlansoprazole

Fig. 8    XRPD of Dexlansoprazole form E

Fig. 9    DSC thermogram of Dexlansoprazole form E

CRYSTALLINE FORMS OF DEXLANSOPRAZOLE

FIELD OF INVENTION

The present invention relates to novel crystalline forms of (R)-2-[[[3-methyl-4(2,2,2-trifluoroethoxy)-2-piridyl]methyl]sulphinyl]benzimidazole (Dexlansoprazole) and the use of a novel crystalline form, in particular hydrated and solvated with ethanol, in a process for the preparation of amorphous Dexlansoprazole.

PRIOR ART

Dexlansoprazole, namely (R)-2-[[[3-methyl-4(2,2,2-trifluoroethoxy)-2-piridyl]methyl]sulphinyl]benzimidazole, is an enantiomer of lansoprazole, a proton pump inhibitor known from WO 92/08716 and used in the treatment of various disorders, such as erosive oesophagitis, gastro-oesophageal reflux and gastrointestinal disorders. EP 1552833 describes Dexlansoprazole in sesquihydrate form, reports that Dexlansoprazole in amorphous form has poor stability, and provides a stable solid composition thereof with a non-toxic base. Dexlansoprazole in amorphous form is known to be more soluble in water than the crystalline form, and consequently possesses greater bioavailability. The use of amorphous Dexlansoprazole is consequently preferred to the crystalline form when preparing solid pharmaceutical compositions.

EP 1552833 reports that amorphous Dexlansoprazole can be obtained by drying a hydrated crystalline form thereof at a temperature between about 20 and 100° C., but the experimental part demonstrates that such drying is actually only performed at a temperature between 60 and 70° C., for a time between 6 and 8 hours. Said process presents numerous drawbacks, mainly correlated with the thermolability of Dexlansoprazole. U.S. Pat. No. 7,285,668, which claims a method of preparing crystalline Dexlansoprazole, confirmed the thermal decomposition of a sample of crystalline Dexlansoprazole.

Hence the preparation of amorphous Dexlansoprazole by heat treatment of a crystalline form of Dexlansoprazole may cause its partial decomposition, leading to low process yields and poor applicability on an industrial scale.

In addition, if the drying conditions are not controlled, there is the risk that instead of an amorphous form a crystalline form is obtained, with a lower water content than the starting form, such as the anhydrous form described in U.S. Pat. No. 6,462,058 and EP 1293507.

There is consequently a need for novel crystalline forms of Dexlansoprazole, possibly hydrated or solvated, which possess improved solubility in water and bioavailability, or are more suitable to be converted to amorphous Dexlansoprazole by a highly efficient method applicable on an industrial scale.

It has now surprisingly been found that Dexlansoprazole can exist in further crystalline forms which can be advantageously used to prepare amorphous Dexlansoprazole by drying at a temperature equal to or less than 50° C.

SUMMARY OF THE INVENTION

The present invention provides novel crystalline forms of (R)-2-[[[3-methyl-4(2,2,2-trifluoroethoxy)-2-piridyl]methyl]sulphinyl]benzimidazole (Dexlansoprazole); in particular: two forms solvated with trifluoroethanol, an anhydrous form, a form hydrated and solvated with ethanol, and a form hydrated and solvated with isopropanol. The invention also provides a process for the preparation of amorphous Dexlansoprazole by making use of the novel crystalline form hydrated and solvated with ethanol.

BRIEF DESCRIPTION OF FIGURES AND ANALYSIS METHODS

The various crystalline modifications of Dexlansoprazole have been characterised by X-ray powder diffraction (XRPD), $^1$H-NMR nuclear magnetic resonance spectrometry, and differential scanning calorimetry (DSC). The water content of the compounds was determined by titration with the Karl Fischer technique. The X-ray diffraction spectra (XRPD) were collected with the APD-2000 automatic powder and liquid diffractometer manufactured by Ital-Structures under the following operating conditions: CuKα radiation ($\lambda$=-1.5418 Å), scanning with a 2θ angle range of 3-40° and a step size of 0.03° for a time of 1 sec. The $^1$H-NMR spectra were acquired with a Varian Mercury 300 spectrometer, using DMSO-d6 as solvent. The DSC thermograms were acquired with a Mettler-Toledo DSC 822e differential scanning calorimeter, under the following operating conditions: open aluminium capsule, range 30-300° C. at the rate of 10° C./min, with nitrogen as purge gas (80 ml/min).

FIG. 9: DSC thermogram of Dexlansoprazole Form E The particle size and $D_{50}$ are determined by the well-known laser light scattering technique, using a Malvern Mastersizer MS1 instrument under the following operating conditions:
  300RF mm lens with 2.4 mm laser beam length;
  500 mg sample dispersed in 10 ml of hexane (ACS reagent) with 1% of SPAN 85®, without pre-sonication, and with a stirring rate of 2500 rpm.

DETAILED DESCRIPTION OF THE INVENTION

Figure 1:
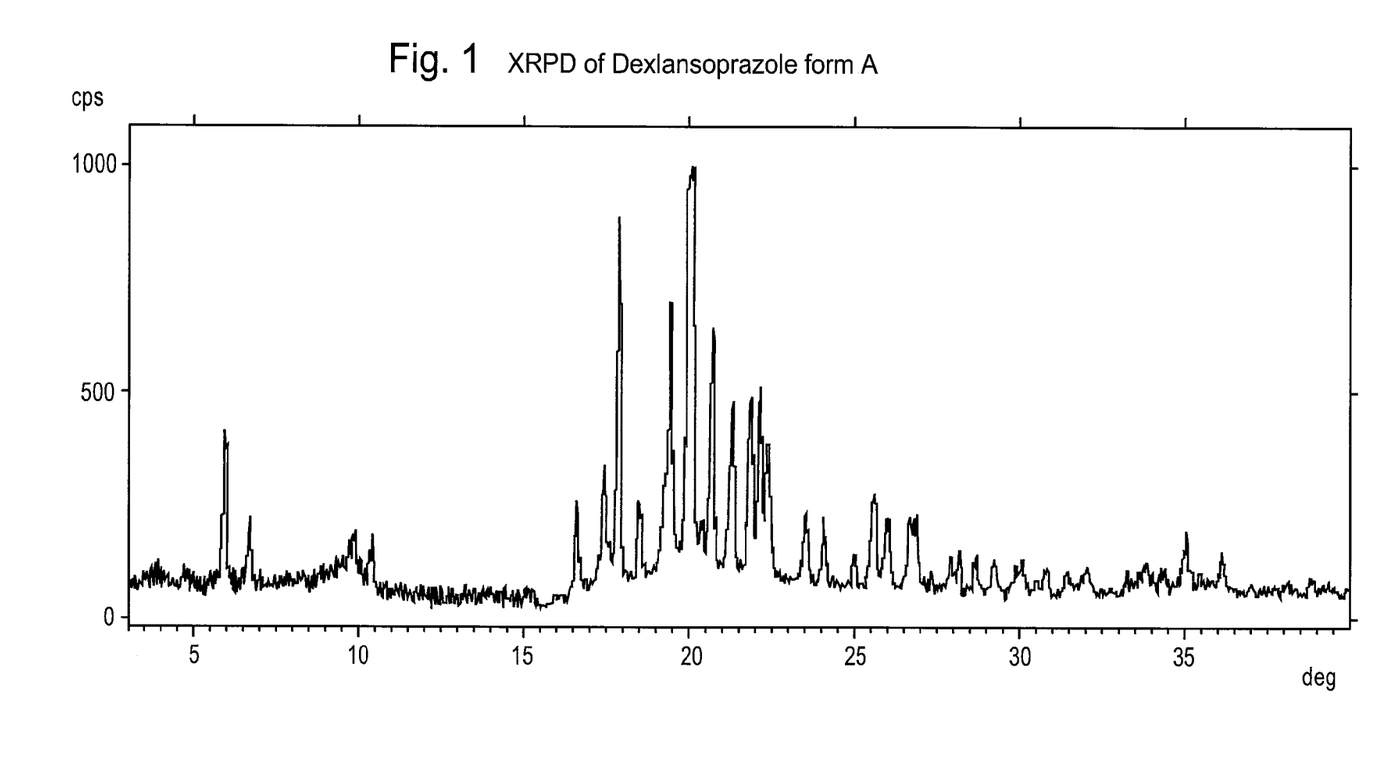
FIG. 1: XRPD spectrum of Dexlansoprazole Form A
Figure 2:
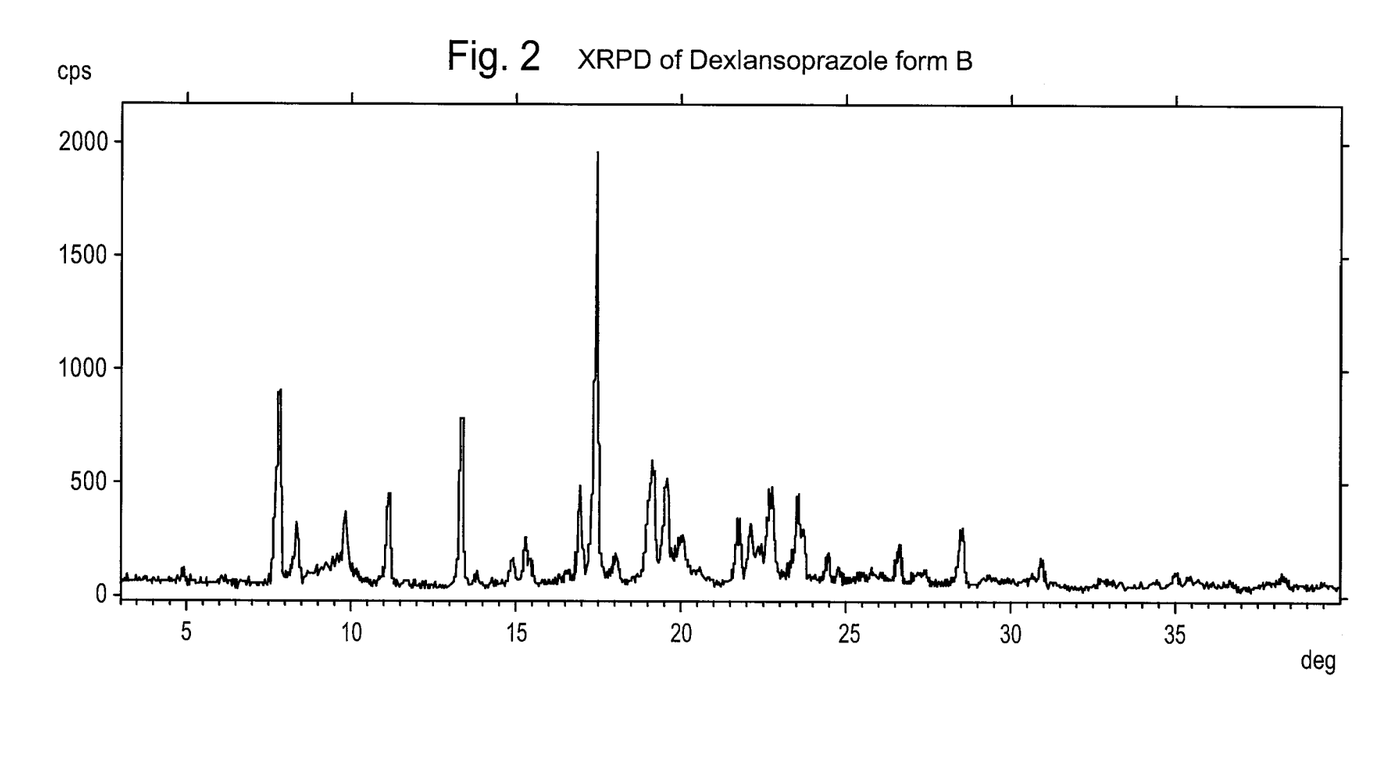
FIG. 2: XRPD spectrum of Dexlansoprazole Form B
Figure 3:
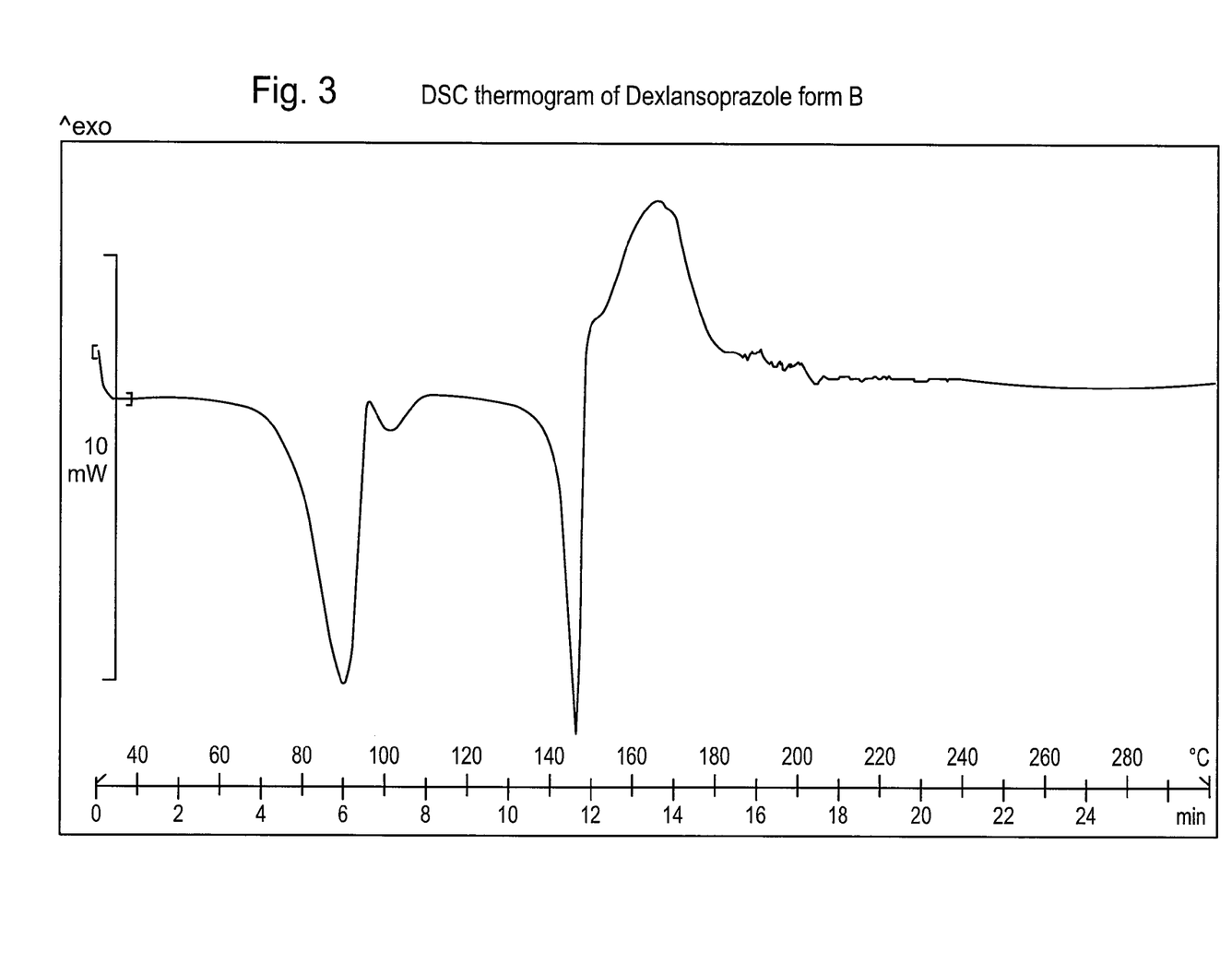
FIG. 3: DSC thermogram of Dexlansoprazole Form B
Figure 4:
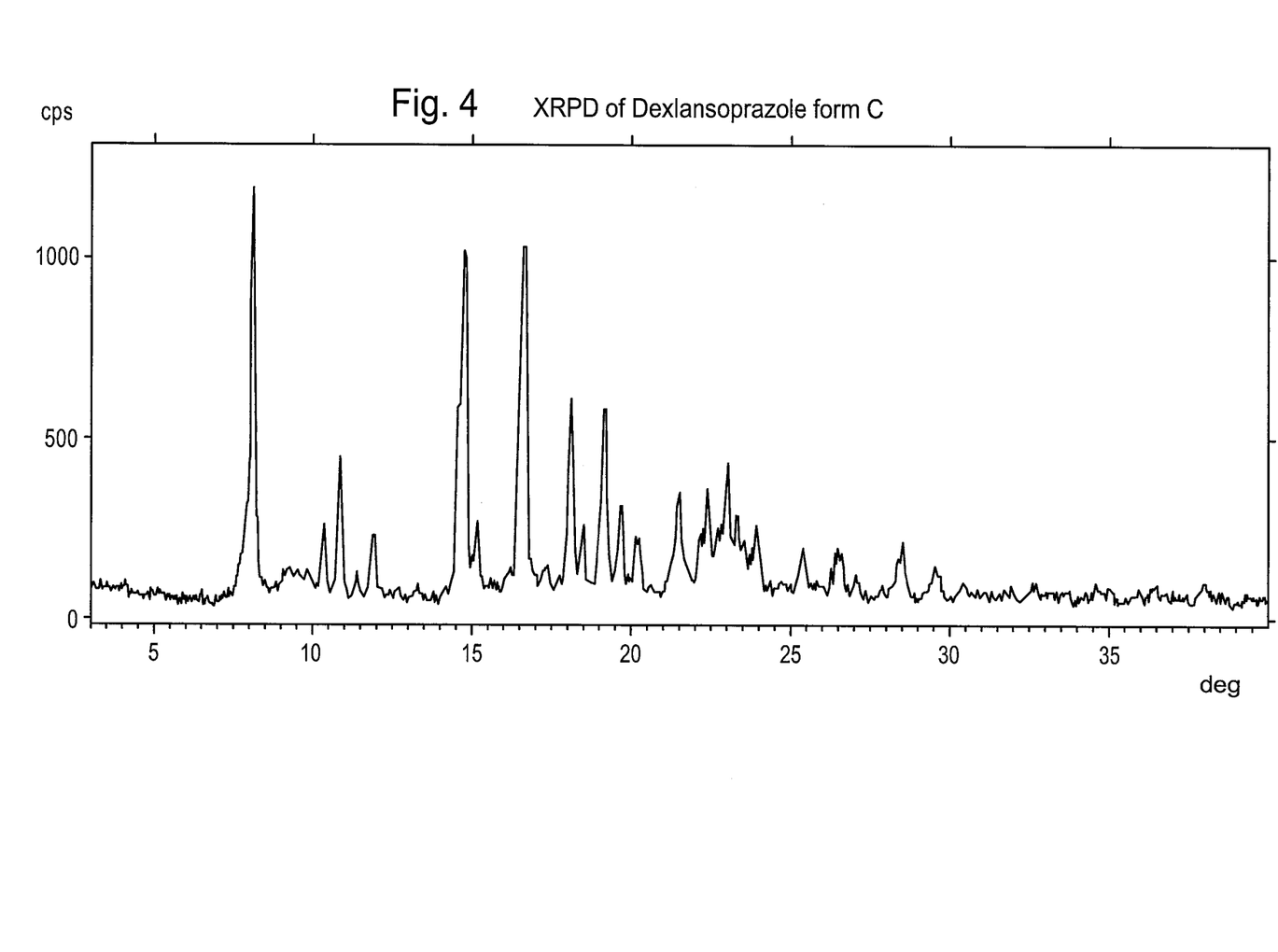
FIG. 4: XRPD spectrum of Dexlansoprazole Form C
Figure 5:
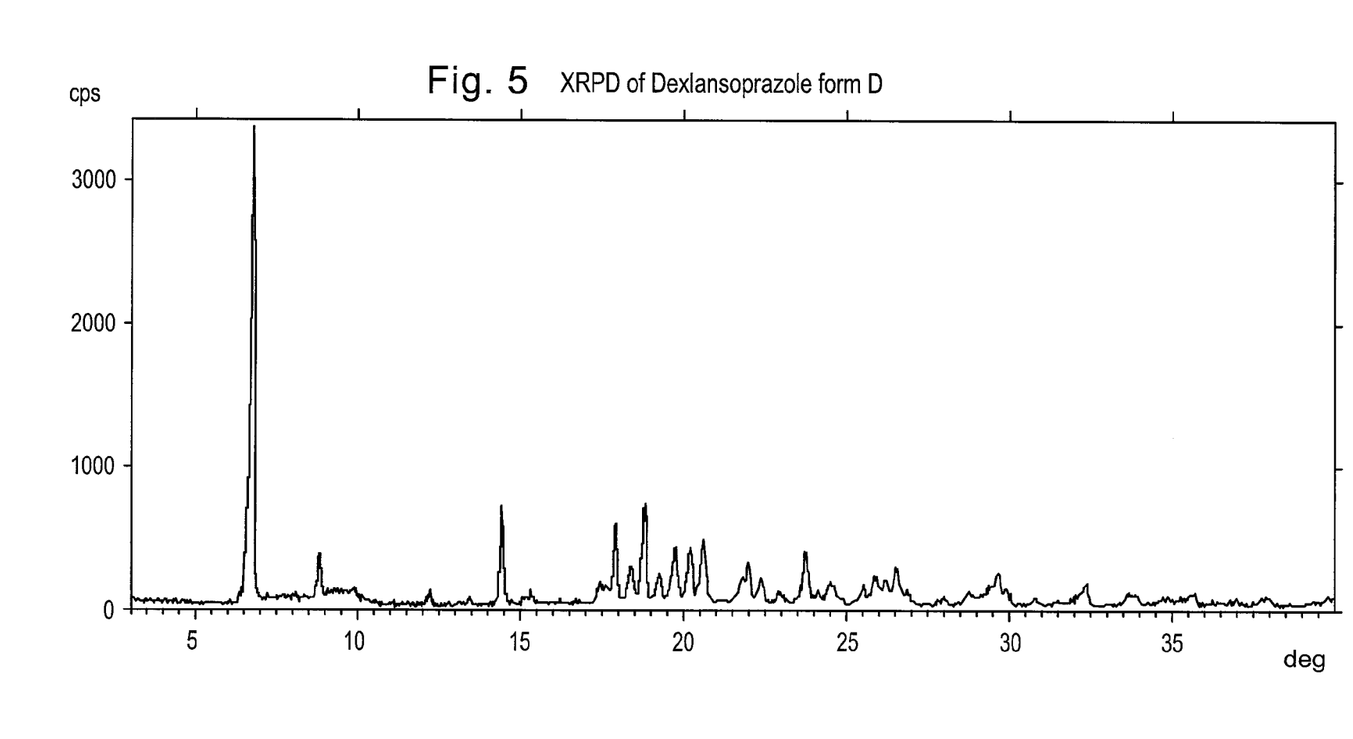
FIG. 5: XRPD spectrum of Dexlansoprazole Form D
Figure 6:
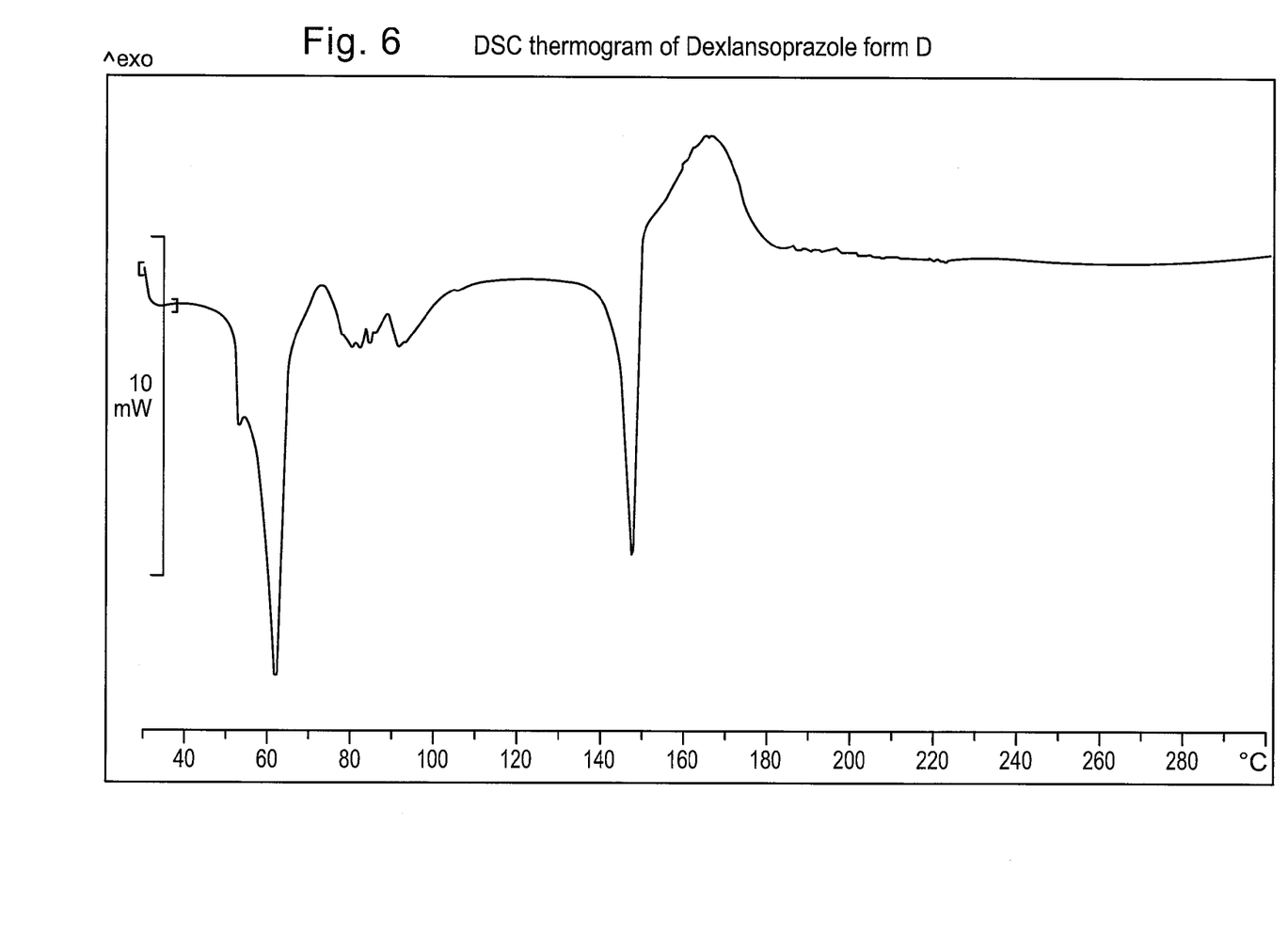
FIG. 6: DSC thermogram of Dexlansoprazole Form D
Figure 8:
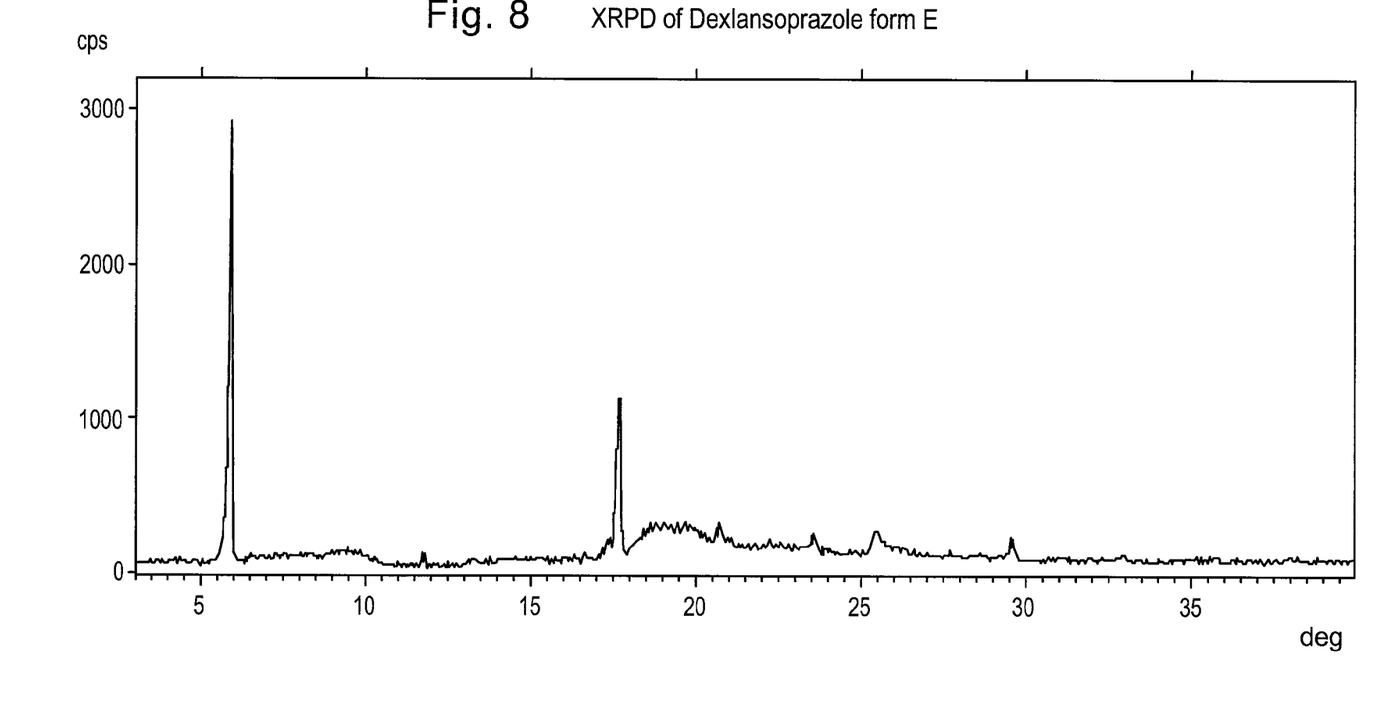
FIG. 8: XRPD spectrum of Dexlansoprazole Form E
Figure 9:
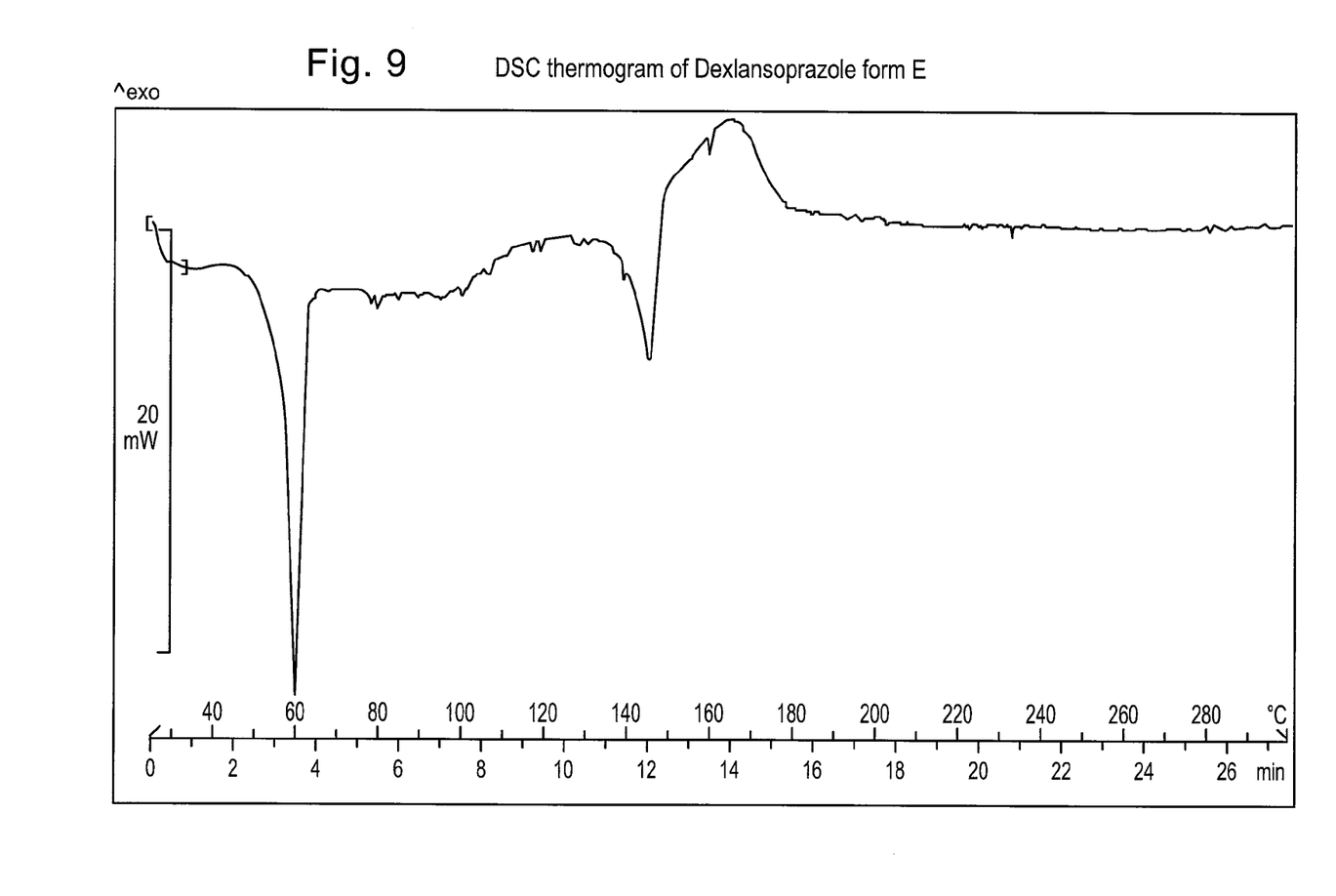

The subject of the present invention is a novel crystalline form of Dexlansoprazole, chosen from:
  a crystalline form, hereafter designated as Form A, with a trifluoroethanol content between about 20 and 50% w/w, preferably between about 30 and about 40%, and more preferably around 35%, so that it can be described as approximately disolvated; a water content between 0 and about 1%, preferably between about 0.2 and about 0.9%, so that it can be described as substantially anhydrous; and characterised by an XRPD substantially as reported in FIG. 1, where the most intense peaks are observed at 6.0, 6.7, 16.6, 17.4, 17.9, 18.5, 19.4, 20.0, 20.7, 21.3, 21.8 and 22.1±0.2° in 2θ;
  a crystalline form, hereafter designated as Form B, with a trifluoroethanol content between about 10 and about 30% w/w, preferably between about 15 and 25%, and more preferably around 20%, so that it can be described as approximately monosolvated; a water content between 0 and about 1%, preferably between about 0.2 and 0.8%, so that it can be described as substantially anhydrous; characterised by an XRPD substantially as reported in FIG. 2, where the most intense peaks are observed at 7.8, 8.3, 9.8, 11.1, 13.3, 15.2, 16.9, 17.4, 19.1, 19.5, 21.8, 22.1 and 23.5±0.2° in 2θ; and having a DSC thermogram as substantially reported in FIG. 3, where the main endothermic peaks are observed at about 90° C. and about 145° C.;

a crystalline form, hereafter designated as Form C, with a water content between 0 and about 1%, preferably between about 0.2 and about 0.7%, so that it can be described as approximately anhydrous; and characterised by an XRPD substantially as reported in FIG. 4, where the most intense peaks are observed at 8.1, 10.3, 10.8, 11.9, 14.7, 15.1, 16.6, 18.1, 19.1, 21.4 and 23.0±0.2° in 2θ.

a crystalline form, hereafter designated as Form D, hydrated and solvated with ethanol, in particular having a water content between about 3 and about 8% w/w, preferably between about 4 and about 6%, and more preferably between about 4.2 and about 5% w/w, so that it can be described as approximately monohydrated; an ethanol content between about 4 and about 8% w/w, preferably between about 5 and about 7% w/w, and more preferably around 6% w/w, so that it can be described as approximately hemisolvated; having an XRPD substantially as reported in FIG. 2, where the most intense peaks are observed at 6.7, 8.8, 12.2, 14.4, 17.9, 18.8, 19.2, 19.7, 20.2, 20.6 and 23.7±0.2° in 2θ; and having a DSC thermogram as substantially reported in FIG. 6, where the main endothermic peaks are observed at about 65° C. and about 145° C.; and a crystalline form, hereafter designated as Form E, hydrated and solvated with isopropanol, in particular having an isopropanol content between about 8 and about 20% w/w, preferably between about 10 and about 16%, so that it can be described as approximately monosolvated; with a water content between about 2 and about 6%, preferably between about 3.5 and about 4.5%, so that it can be described as approximately monohydrated; having an XRPD substantially as reported in FIG. 8, where the most intense peaks are observed at 5.9, 17.3, 17.7, 18.8, 20.7, 23.6, 25.5 and 29.7±0.2° in 2θ; and having a DSC thermogram as substantially reported in FIG. 9. The main endothermic peaks are observed at about 60° C. and about 145° C.

Dexlansoprazole in crystalline form A, as defined here, can be obtained by a process comprising:
Dispersion of Dexlansoprazole in trifluoroethanol or a mixture thereof with at least a further solvent, and dissolution thereof;
Rapid cooling of the solution so that crystalline form A precipitates; and
Recovery of the solid.

Dexlansoprazole, used as starting material, may be any crystalline form of Dexlansoprazole free base, either anhydrous or hydrated, but preferably anhydrous. The term "hydrated" here relates to a form with any degree of hydration, in particular hemihydrate or sesquihydrate.

Trifluoroethanol can be mixed with at least an additional solvent.

An additional solvent can be for example, one to four, preferably one or two solvents chosen from the group comprising ethers, such as THF; $C_1$-$C_6$ alkanols, such as methanol, ethanol or isopropanol; $C_3$-$C_6$ ketones, such as acetone, methyl ethyl ketone, and methyl isobutyl ketone; $C_2$-$C_6$ alkyl esters, such as ethyl acetate or isopropyl acetate; cyclic or acyclic aliphatic hydrocarbons, such as hexane and heptane; aromatic hydrocarbons, such as toluene; and polar protic solvents, such as water.

The Dexlansoprazole concentration in the starting dispersion can be between about 2 and 50% w/w, preferably between about 20 and 40% w/w.

The Dexlansoprazole can preferably be dissolved in the starting dispersion by heating to a temperature between about 25 and about 50° C., more preferably between about 30 and about 40° C. The solution can be cooled, preferably at about 10-20° C. a minute, to a temperature between −10 and 20° C., in particular about 0° C., so that crystalline form A precipitates. Crystallisation may be triggered by adding crystals of Dexlansoprazole in crystalline form A, previously obtained.

Dexlansoprazole in crystalline form A can be recovered by known methods, such as filtration or centrifugation, preferably by filtration through a Bückner filter. If desired, a solvent chosen from the group of acyclic aliphatic hydrocarbons, such as hexane or heptane, or cyclic aliphatic hydrocarbons, such as cyclohexane, can be added to the dispersion containing the precipitate to facilitate the recovery of the solid.

Dexlansoprazole in crystalline form B can be obtained by a process comprising:
Dispersion of Dexlansoprazole in trifluoroethanol or a mixture thereof with at least an additional solvent, and dissolution thereof;
Slow cooling of the solution so that crystalline form B precipitates; and
Recovery of the solid.

Dexlansoprazole, used as starting material, can be any crystalline form of Dexlansoprazole free base, either anhydrous or hydrated, but preferably anhydrous.

Trifluoroethanol can be mixed with at least a further solvent, for example one to four, preferably one or two solvents, chosen from the group of the additional solvents indicated above.

The Dexlansoprazole concentration in the starting dispersion can be between about 2 and about 50% w/w, preferably between about 20 and about 40% w/w.

The Dexlansoprazole can preferably be dissolved in the starting dispersion by heating to a temperature between about 25 and about 50° C., more preferably between about 30 and about 40° C. The solution can be cooled, preferably at about 1° C. a minute, to obtain precipitation of crystalline form B, to a temperature between −10 and 20° C., in particular about 0° C.; crystallisation may be triggered by adding crystals of Dexlansoprazole in crystalline form B, previously obtained.

Dexlansoprazole in crystalline form B can be recovered by known methods such as filtration or centrifugation, preferably by filtration through a Bückner filter. If desired, an apolar aprotic solvent such as acetonitrile can be added to the dispersion containing the precipitate to facilitate recovery of the solid. Dexlansoprazole in crystalline form B, as defined here, presents a DSC thermogram as substantially reported in FIG. 3, where the endothermic peak at about 90° C. indicates the desolvation of trifluoroethanol, and the subsequent endothermal peak at about 145° C. indicates a melting process.

Dexiansoprazole in crystalline form C can be obtained by a process comprising:
Drying of Dexiansoprazole in crystalline form B, as defined here, at a temperature equal to or lower than 60° C.; and
Recovery of the solid.

The drying temperature may be between about 5 and about 60° C., preferably between about 20 and about 45° C., and more preferably between about 30 and about 40° C.

Drying can be performed at low pressure, typically between 0.1 and 500 mmHg, preferably between 1 and 100 mmHg, and more preferably around 10 mmHg or under air and/or nitrogen flow. The drying time can range from a few hours to several days, depending on the temperature and pressure.

Dexlansoprazole in crystalline form D can be obtained by a process comprising:

Dispersion of Dexiansoprazole in ethanol or a mixture thereof with at least a further solvent, and dissolution thereof;

Cooling of the solution so that crystalline form D precipitates; and

Recovery of the solid.

Dexlansoprazole, used as starting material, may be any crystalline form of Dexlansoprazole free base, either anhydrous or hydrated, but preferably hydrated.

Ethanol can be mixed with at least an additional solvent, for example one to four, but preferably one or two solvents, chosen from the group indicated above.

The Dexlansoprazole concentration in the starting dispersion can be between about 2 and about 50% w/w, preferably between about 20 and about 40% w/w.

Dexlansoprazole can be dissolved in the starting dispersion preferably by heating it to a temperature between about 20 and about 50° C., more preferably between about 30 and about 40° C.

Cooling of the solution to obtain precipitation of crystalline form D can be effected at a temperature between −10 and 20° C., in particular at about 0° C.; crystallisation may be triggered by adding crystals of the Dexlansoprazole in crystalline form D, previously obtained.

Dexlansoprazole in crystalline form D can be recovered by known methods such as filtration or centrifugation, preferably by filtration, followed by drying at low pressure, typically between 0.1 and 500 mmHg, preferably between 1 and 100 mmHg, and more preferably around 10 mmHg and/or under air and/or nitrogen flow. The drying temperature is preferably maintained at about 20° C. Dexlansoprazole in crystalline form D, as defined here, presents a DSC thermogram as substantially reported in FIG. 6, where the endothermic peak at about 65° C. indicates the desolvation of trifluoroethanol, and the subsequent endothermal peak at about 145° C. indicates a melting process.

Dexlansoprazole in crystalline form E can be prepared by a process comprising:

Dispersion of Dexlansoprazole in isopropanol or a mixture thereof with at least an additional solvent, and dissolution thereof;

Rapid cooling of the solution to promote precipitation of crystalline form E; and Recovery of the solid.

Dexlansoprazole, used as starting material, may be any crystalline form of Dexlansoprazole free base, either anhydrous or hydrated, but preferably hydrated.

The isopropanol can be mixed with at least an additional solvent, for example one to four, but preferably one or two solvents, chosen from the group indicated above.

The Dexlansoprazole concentration in the starting dispersion can be between about 2 and about 50% w/w, preferably between about 10 and about 30% w/w.

Dexlansoprazole is preferably dissolved in the starting dispersion by heating it to a temperature between about 20 and about 50° C., and more preferably between about 30 and about 40° C.

The precipitation of crystalline form E can be achieved by cooling to a temperature between about −10 and about 20° C., preferably to about 0° C., possibly triggering the reaction with crystals of crystalline form E, previously obtained. The term "rapid cooling" means cooling at a rate typically between about 10 and about 20° C./minute.

Dexlansoprazole in crystalline form E can be recovered by known methods, as illustrated above. If desired, an apolar aprotic solvent, for example one chosen from the group of acyclic hydrocarbons, such as hexane or cyclohexane, or cyclic hydrocarbons, such as toluene, can be added to the dispersion containing the precipitate to facilitate the recovery of the solid.

Dexlansoprazole in crystalline form E, as defined here, presents a DSC thermogram as substantially reported in FIG. 9, where the endothermic peak at about 60° C. indicates the desolvation of isopropanol, and a peak at about 145° C. indicates a melting process.

A further object of the present invention is a process for the preparation of amorphous Dexlansoprazole which comprises:

Drying of crystalline form D, as defined here, at a temperature equal to or lower than 50° C.; and Recovery of the solid.

Drying is preferably performed at a low enough temperature to ensure that thermal decomposition of Dexlansoprazole does not occur, for example between about 5 and 50° C., preferably between about 20 and about 40° C., and more preferably between about 30 and about 40° C., in particular at about 35° C.; and at low pressure, typically between 0.1 and 500 mmHg, preferably between 1 and 100 mmHg, and more preferably around 10 mmHg, and/or under air and/or nitrogen flow.

The drying time can range from a few hours to several days, depending on the temperature and pressure.

The solid can be recovered in accordance with known methods.

Figure 7:
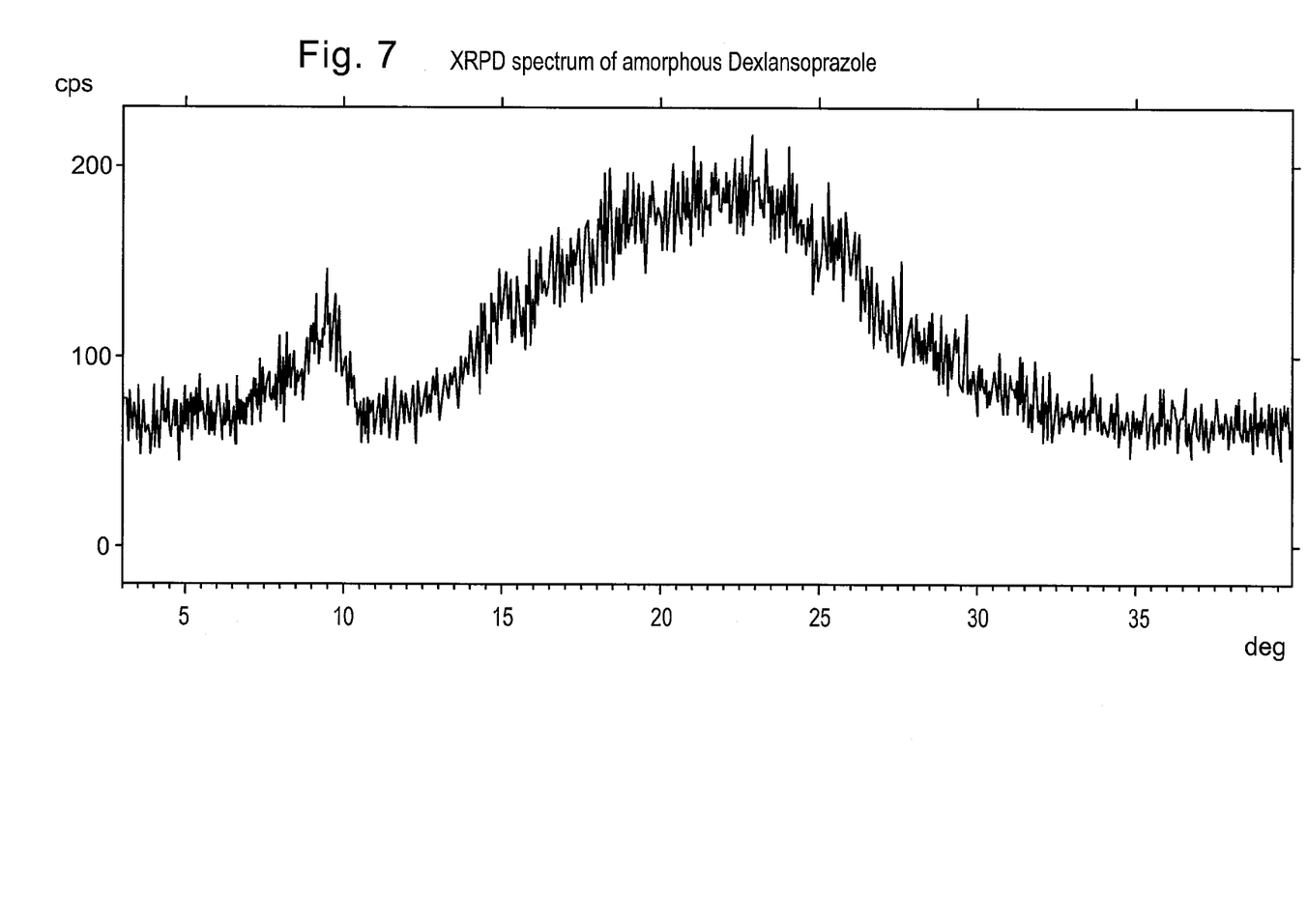
FIG. 7: XRPD spectrum of amorphous Dexlansoprazole

The amorphous Dexlansoprazole thus obtained presents an XRPD spectrum as substantially reported in FIG. 7.

The water content of the amorphous solid thus obtained depends on the water content present in the starting Dexlansoprazole compound in crystalline form D, and on the time required for its complete conversion to the amorphous form. The water content of the amorphous solid obtained by the present method generally ranges from 0 to about 4.5%.

The size of the crystals of Dexlansoprazole Forms A, B, C, D and E, as defined here, and the fragments of amorphous Dexlansoprazole obtained in accordance with the invention, is characterised by a $D_{50}$ value between about 25 and about 250 μM. If desired, said value can be reduced by micronisation or fine grinding.

Dexlansoprazole in Forms A, B, C, D and E and amorphous Dexlansoprazole, as obtainable by the process according to the invention, has a degree of purity equal to or greater than 99.9%; in other words, its quality is suitable to meet the regulatory requirements for products designed for therapeutic use.

Dexlansoprazole in Form A, B, C, D or E, like Dexlansoprazole in known forms, is useful in the treatment of the same gastroenteric disorders.

The invention also relates to a pharmaceutical composition comprising a diluent and/or vehicle and, as active ingredient, Dexlansoprazole in at least one, and typically one or two, of the novel Forms A, B, C, D and E. If desired, said composition can also contain, as active ingredient, at least one of the known forms of Dexlansoprazole cited above, in particular the amorphous form.

The choice of ratio between the quantity of one or more of Forms A, B, C, D, and E of Dexlansoprazole and of Dexlansoprazole in one or more of the known forms depends on their physical and biological properties, and is left to the discretion of those skilled in the art.

The pharmaceutical compositions according to the invention can be formulated in a variety of forms suitable for administration to humans or animals, in accordance with known techniques. For example, they may take the form of capsules, tablets, dragées or other known forms.

The following examples illustrate the invention.

Example 1

Preparation of Dexlansoprazole, Form A 1.6 g of anhydrous Dexlansoprazole is suspended in 5 ml of trifluoroethanol, and the dispersion is heated to 35-40° C. until completely dissolved. The dispersion is then rapidly cooled to 0° C., and a solid precipitates. The solid, which is 99.7% pure, is recovered by filtration through a Bückner filter.

XRPD: Main peaks at 6.0, 6.7, 16.6, 17.4, 17.9, 18.5, 19.4, 20.0, 20.7, 21.3, 21.8 and 22.1±0.2° in 2θ.

$H^1$-NMR (in DMSO): d (1H), 8.27 ppm; m (2H), 7.6 ppm; dd (2H), 7.27-7.30 ppm; d (1H), 7.07 ppm; broad t (2H), 6.05 ppm; q (2H), 4.84-4.92 ppm; q (2H), 4.72-4.84 ppm; m (4H), 3.75-3.95 ppm; s (3H). 2.16 ppm.

Example 2

Preparation of Dexlansoprazole, Form B 2.0 g of anhydrous Dexlansoprazole is dispersed in 5 ml of acetonitrile and 3 ml of trifluoroethanol. The dispersion is heated to 35° C. until completely dissolved. The solution is cooled slowly to about 0° C., and a pale solid precipitates. The dispersion is filtered through a Bückner filter to recover the solid, which is 99.8% pure.

XRPD: Main peaks at 7.8, 8.3, 9.8, 11.1, 13.3, 15.2, 16.9, 17.4, 19.1, 19.5, 21.8, 22.1 and 23.5±0.2° in 2θ.

The product shows a DSC thermogram as reported in FIG. 3.

$H^1$-NMR (in DMSO): d (1H), 8.27 ppm; m (2H), 7.6 ppm; dd (2H), 7.27-7.30 ppm; d (1H), 7.07 ppm; broad t (0.5H), 6.05 ppm; q (2H), 4.84-4.92 ppm; q (2H), 4.72-4.84 ppm; m (1H), 3.75-3.95 ppm; s (3H). 2.16 ppm.

Example 3

Preparation of Dexlansoprazole, Form C

Dexlansoprazole form B is stove-dried at 40-45° C. at low pressure for about 10 h. The solid recovered is 99.9% pure.

XRPD: Main peaks at 8.1, 10.3, 10.8, 11.9, 14.7, 15.1, 16.6, 18.1, 19.1, 21.4 and 23.0±0.2° in 2θ.

$H^1$-NMR (in DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; s (3H). 2.16 ppm.

Example 4

Preparation of Dexlansoprazole, Form D 2 g of Dexlansoprazole sesquihydrate is dissolved in 4 ml of absolute ethanol at about 30° C. The solution thus obtained is cooled to 0° C. A white solid precipitates. The dispersion is diluted with a further 4 ml of ethanol and filtered through a Bückner filter. The solid recovered is dried under vacuum at room temperature. The solid recovered is 99.7% pure.

XRPD: Main peaks at 6.7, 8.8, 12.2, 14.4, 17.9, 18.8, 19.2, 19.7, 20.2, 20.6 and 23.7° in 2θ.

The product shows a DSC thermogram as reported in FIG. 6.

$H^1$-NMR (in DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; t (0.5 H), 4.38 ppm; m (1H), 3.4 ppm; s (3H). 2.16 ppm; t (1.5 H), 1.05 ppm.

Example 5

Preparation of Dexlansoprazole, Form D 2 g of Dexlansoprazole sesquihydrate is dissolved in 5 ml of ethanol at room temperature. A solid precipitates at room temperature. The dispersion is diluted with 4 ml of toluene and cooled to 0° C. A further 2 ml of toluene are added, and the solution is filtered through a Bückner filter. The solid is left to dry on the filter. The solid recovered is 99.8% pure.

XRPD: Main peaks at 6.7, 8.8, 12.2, 14.4, 17.9, 18.8, 19.2, 19.7, 20.2, 20.6 and 23.7° in 2θ.

The product shows a DSC thermogram as reported in FIG. 6.

$H^1$-NMR (in DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; t (0.5 H), 4.38 ppm; m (1H), 3.4 ppm; s (3H). 2.16 ppm; t (1.5 H), 1.05 ppm.

Example 6

Preparation of Dexlansoprazole, Form D 3 g of Dexlansoprazole sesquihydrate is dissolved in 6 ml of ethanol at room temperature. A solid forms after a few minutes. 3 ml of ethanol are added; the dispersion is then cooled to 0° C. and 3 ml of isopropanol are added. The solution is filtered through a Bückner filter and dried under vacuum at room temperature. The solid recovered is 99.7% pure.

XRPD: Main peaks at 6.7, 8.8, 12.2, 14.4, 17.9, 18.8, 19.2, 19.7, 20.2, 20.6 and 23.7° in 2θ.

The product shows a DSC thermogram as reported in FIG. 6.

$H^1$-NMR (in DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; t (0.5 H), 4.38 ppm; m (1H), 3.4 ppm; s (3H). 2.16 ppm; t (1.5 H), 1.05 ppm.

Example 7

Preparation of Dexlansoprazole, Form D 4 g of Dexlansoprazole sesquihydrate is dissolved in 12 ml of ethanol at about 35° C. The dispersion is cooled to 0° C. and seeded with crystalline Dexlansoprazole in monohydrate form hemisolvated with ethanol, and 20 ml of heptane are added. The pale solid that precipitates is filtered through a Bückner filter and dried on the filter. The solid recovered is 99.8% pure.

XRPD: Main peaks at 6.7, 8.8, 12.2, 14.4, 17.9, 18.8, 19.2, 19.7, 20.2, 20.6 and 23.7° in 2θ.

The product shows a DSC thermogram as reported in FIG. 6.

$H^1$—NMR (in DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; t (0.5 H), 4.38 ppm; m (1H), 3.4 ppm; s (3H). 2.16 ppm; t (1.5 H), 1.05 ppm.

Example 8

Preparation of Dexlansoprazole, Form D 8.8 g of Dexlansoprazole sesquihydrate is dissolved in 20 ml of ethanol at about 35° C. The dispersion is cooled to 0° C., and a pale solid precipitates. 30 ml of hexane are added. The dispersion is filtered through a Bückner filter and dried on the filter. Dexlansoprazole form D is recovered with a 91% yield and 99.7% purity.

XRPD: Main peaks at 6.7, 8.8, 12.2, 14.4, 17.9, 18.8, 19.2, 19.7, 20.2, 20.6 and 23.7° in 2θ.

The product shows a DSC thermogram as reported in FIG. 6.

$H^1$-NMR (in DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; t (0.5 H), 4.38 ppm; m (1H), 3.4 ppm; s (3H). 2.16 ppm; t (1.5 H), 1.05 ppm.

Example 9

Preparation of Amorphous Dexlansoprazole 4 g of Dexlansoprazole sesquihydrate is dissolved in 16 ml of ethanol at about 30° C. The solution is cooled to 0° C. and seeded with crystalline Dexlansoprazole in monohydrate form hemisolvated with ethanol (Form D). A white solid precipitates. The dispersion is diluted with 4 ml of ethanol and filtered through a Bückner filter. It is then stove-dried at 35° C. for about 5 h, and amorphous Dexlansoprazole with a purity of 99.9% is recovered.

XRPD: no detectable diffraction peak.

$H^1$-NMR (in DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; s (3H). 2.16 ppm.

Example 10

Preparation of Amorphous Dexlansoprazole from Dexlansoprazole form D 5 g of crystalline Dexlansoprazole in monohydrate form hemisolvated with ethanol (form D) is stove-dried overnight at about 30° C. Amorphous Dexlansoprazole with a purity of 99.8% is obtained.

XRPD: no detectable diffraction peak.

$H^1$-NMR (in DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; s (3H). 2.16 ppm.

Example 11

Preparation of Dexlansoprazole Form E 4 g of Dexlansoprazole sesquihydrate is dispersed in 20 ml of isopropanol, and the dispersion is heated at 35° C. until dissolution is complete. It is then cooled to 0° C. at the rate of about 10° C./minute. A solid with 99.7% purity precipitates, and is recovered by filtration.

XRPD: Main peaks at 5.9, 17.3, 17.7, 18.8, 20.7, 23.6, 25.5 and 29.7±0.2° in 2θ.

The product shows a DSC thermogram as reported in FIG. 9.

$H^1$-NMR (in DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; d (1H), 4.3 ppm; m (1H), 3.7-3.8 ppm; s (3H). 2.16 ppm; d (6H), 1.05 ppm.

The invention claimed is:

1. A process for preparing amorphous Dexlansoprazole comprising:
   drying Dexlansoprazole in crystalline form D having a water content ranging from about 3 to 8% w/w, an ethanol content ranging from about 4 to 8% w/w, having an XPRD wherein the most intense peaks fall at 6.7, 8.8, 12.2, 14.4, 17.9, 18.8, 19.2, 19.7, 20.2, 20.6 and 23.7±0.2° in 2θ, and having a DSC thermogram wherein the main endothermic peaks fall at about 65° C. and at about 145° C., at a temperature equal to or lower than 50° C., and
   recovering dried solid amorphous Dexlansoprazole.

2. Process according to claim 1, wherein the drying is carried out at a temperature low enough to prevent thermal decomposition of Dexlansoprazole.

3. Process according to claim 2 wherein the drying is carried out at a temperature ranging from 5 to 50° C.

4. Process according to claim 2 wherein the drying is carried out under reduced pressure.

5. Process according to claim 4 wherein the drying is carried out between 0.1 and 500 mmHg and/or under air and/or nitrogen flow.

* * * * *